(12) United States Patent
Adams et al.

(10) Patent No.: US 6,365,672 B1
(45) Date of Patent: Apr. 2, 2002

(54) POLYSILOXANE BLOCK COPOLYMERS IN TOPICAL COSMETIC AND PERSONAL CARE COMPOSITIONS

(75) Inventors: Gerald Adams; Ezat Khoshdel; Anthony Moretta; Yvonne Christine Plant; Euan Stuart Reid, all of Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/575,966

(22) Filed: May 23, 2000

(30) Foreign Application Priority Data

May 24, 1999 (GB) ............................................. 9912073

(51) Int. Cl.$^7$ ............................ C08L 83/10; A61K 7/06
(52) U.S. Cl. ....................... 525/101; 525/100; 525/102; 525/106; 514/63; 424/70.1; 424/70.12; 424/70.122; 424/401
(58) Field of Search ................................ 525/100, 101, 525/102, 106; 514/63; 424/401, 70.1, 70.12, 70.122

(56) References Cited

U.S. PATENT DOCUMENTS

| 5,468,477 | A | * | 11/1995 | Kumar et al. | 424/78.17 |
| 5,840,291 | A | * | 11/1998 | Tsubakihara et al. | 424/70.12 |
| 5,965,115 | A | * | 10/1999 | Bolich, Jr. et al. | 424/70.12 |
| 5,986,015 | A | * | 11/1999 | Midha et al. | 525/370 |
| 6,093,410 | A | * | 7/2000 | Peffly et al. | 424/401 |

FOREIGN PATENT DOCUMENTS

| EP | 0992519 | 4/2000 |
| WO | 98/01480 | 1/1998 |
| WO | 98/40415 | 9/1998 |
| WO | 98/48771 | 11/1998 |
| WO | 98/51261 | 11/1998 |

OTHER PUBLICATIONS

Search Report under Section 17, Application No. GB 99/12073.5 dated September 3, 1999.
International Search Report Application No. PCT/EP 00/04429 mailed Oct. 4, 2000.
Nakagawa Y. et al. "Development of a Novel Attachable Initiators for Atom Transfer Radical Polymerization. Synthesis of Block and Graft Copolymers from Poly(dimethylsiloxane) Macroinitiators" Polymer, GB, Elsevier Science Publishers B.V. vol. 39. No. 21.

* cited by examiner

Primary Examiner—Robert Dawson
Assistant Examiner—Jeffrey B. Robertson
(74) Attorney, Agent, or Firm—Matthew Boxer

(57) ABSTRACT

A process for making a polysiloxane block copolymer which is built up from units of the formula [A] [B], in which A is a polymeric block built up from radically polymerisable monomer, and B is a polysiloxane block, the process comprising the steps of polymerising a radically polymerisable monomer in the presence of an atom transfer radical initiator to form an polymer which is end-functionalized with a leaving group capable of nucleophilic substitution by nucleophilic end-groups on a polysiloxane, and reacting the polymer with a polysiloxane having nucleophilic end-groups so that a polysiloxane block copolymer is formed via a nucleophilic displacement reaction between the end-groups on the polysiloxane and leaving groups on the polymer respectively. Also provided is a cosmetic and personal care composition, such as a hair styling composition, comprising the polysiloxane block copolymer as described above.

6 Claims, No Drawings

POLYSILOXANE BLOCK COPOLYMERS IN TOPICAL COSMETIC AND PERSONAL CARE COMPOSITIONS

FIELD OF THE INVENTION

The present invention relates to polysiloxane block copolymers suitable for use in cosmetic and personal care compositions, their preparation, and to cosmetic and personal care compositions, such as hair styling compositions, containing the polysiloxane block copolymers.

BACKGROUND AND PRIOR ART

Cosmetic and personal care compositions such as hair styling sprays, mousses, gels and shampoos, frequently contain resins, gums and adhesive polymers to provide a variety of benefits, for example, film-forming ability, thickening, sensory properties and hair shaping and setting.

Polymers for use in such compositions include organic or silicone-containing linear or graft copolymers which contain various monomers in an alternating, random, block or homopolymer configuration.

Graft copolymers are known for use as film-forming polymers in hair care and other personal care compositions. These graft copolymers typically comprise a polymeric backbone and one or more macromonomers grafted to the backbone, in which the physical and chemical attributes such as glass transition temperature and water solubility can be selected independently for the polymeric backbone and macromonomer grafts in order to provide the desired overall polymer properties.

For example, WO95/01383 and WO95/01384 describe the use of water or alcohol soluble or dispersible graft copolymers in hair and skin care compositions, in which the copolymer has a backbone and two or more polymeric side chains, and is formed by copolymerisation of randomly repeating monomer units A and B. Monomer A is selected to have a hydrophobic character and macromonomer B comprises a long hydrophilic part. EP 412,704, EP 408,313 and EP 412,707 have suggested the use of silicone grafted acrylate copolymers in hair care applications. U.S. Pat. No. 4,988,506 describes the use of non-pressure sensitive polysiloxane-grafted copolymers in hair care compositions.

Block copolymers have an advantage over graft copolymers in that the polymer architecture can be controlled more closely. This is particularly important when designing polymers with segments of distinct physical and chemical properties for particular applications, e.g. alternating "hard" and "soft" segments in a hairspray polymer for improved hold and feel.

U.S. Pat. No. 5,468,477 describes cosmetics and personal care compositions containing a vinyl-silicone graft or block copolymer comprising a silicone polymer segment and a vinyl polymer segment. This block or graft copolymer is prepared by the free radical polymerisation of a mercapto functional silicone chain transfer agent and vinyl monomers. Copolymers prepared by this method generally have a low molecular weight and a low silicone content due to premature chain termination. Also, intramolecular cross-linking reactions lead to polymer build up in an uncontrolled manner, and hence polydisperse systems with a mixture of chain lengths and molecular architectures. Furthermore, the presence of mercapto groups is a disadvantage in personal care applications since they tend to decompose to give odour problems.

Another approach to the synthesis of block copolymers is to use organopolysiloxane macroinitiators, which are organopolysiloxanes which contain groups which form radicals. These are described in U.S. Pat. No. 5,523,365 and used in WO98/48771, where a polydimethylsiloxane macroinitiator with azo groups is used to synthesise a block copolymer. Problems include the expense and safety hazards associated with the radical macroinitiator, which has to present in significant quantities, otherwise there will be insufficient siloxane content in the final product. Furthermore, the size of the polydimethylsiloxane macroinitiator means that the reaction is inefficient, and large quantities of unreacted silicone have to be removed in a time-consuming extraction process that would be extremely difficult to scale up.

A need exists for conveniently prepared and cost-effective polysiloxane block copolymers for use in cosmetics and personal care compositions.

The present invention provides an improved process for making polysiloxane block copolymers in which end-functionalised polymers are prepared using atom transfer radical polymerisation and then reacted with organopolysiloxanes using a simple nucleophilic displacement reaction, to prepare polysiloxane block copolymers of controlled architecture. Atom transfer radical polymerisation is described in general in *Polymer* Vol 39, No.21, pp 5163–5170 (Nakagawa et al) and used in WO98/51261 to make graft copolymers.

SUMMARY OF THE INVENTION

In a first aspect, the present invention provides a process for making a polysiloxane block copolymer which is built up from units of the formula [A][B], in which A is a polymeric block built up from radically polymerisable monomer, and B is a polysiloxane block, the process comprising the steps of polymerising a radically polymerisable monomer in the presence of an atom transfer radical initiator to form an polymer which is end-functionalised with a leaving group capable of nucleophilic substitution by nucleophilic end-groups on a polysiloxane, and reacting the polymer with a polysiloxane having nucleophilic end-groups so that a polysiloxane block copolymer is formed via a nucleophilic displacement reaction between the end-groups on the polysiloxane and leaving groups on the polymer respectively.

In a second aspect, the invention provides a polysiloxane block copolymer which is obtainable by the process described above.

The invention also provides a cosmetic and personal care composition, such as a hair styling composition, comprising the polysiloxane block copolymer as described above.

DETAILED DESCRIPTION AND PREFERRED EMBODIMENTS

Process

The process of the present invention comprises two key reaction steps:

First Reaction Step

The first reaction step involves polymerising a radically polymerisable monomer in the presence of an atom transfer radical initiator to form an polymer which is end-functionalised with a leaving group capable of nucleophilic substitution by nucleophilic end-groups on a polysiloxane. By "end-functionalised" and "end-group" is meant that the group is at or near a terminal position of the polymer and polysiloxane respectively.

Typically, the atom transfer radical initiator comprises at least one —C(O)X group, in which X is a leaving group capable of substitution by a nucleophilic O, N or S atom on the polysiloxane in the second reaction step, and at least one organic halide group capable of generating a radical in the presence of a transition metal catalyst.

Examples of preferred atom transfer radical initiators have the formula:

$$R^1—C(O)X$$

where $R^1$ is the organic halide group and X is the leaving group. Preferably X is a halogen atom (F, Cl, Br or I). By "organic halide group" is meant any linear, branched or cyclic (aromatic or otherwise) carbon structure, whether substituted or unsubstituted,, which also contains a halogen atom (F, Cl, Br or I).

Preferred radical initiators have the general formula:

$$C(R^2)(R^3)Hal'—(R^4)_r—C(O)Hal$$

where Hal' and Hal independently denote halogen atoms, $R^2$ and $R^3$ are independently selected from hydrogen or a monovalent, optionally substituted, linear or branched $C_{1-18}$ hydrocarbon radical, r is an integer having a value of 0 or 1, and $R^4$ is selected from divalent, optionally substituted, linear or branched $C_1–C_{18}$ hydrocarbon radicals.

Examples of monovalent, unsubstituted radicals are alkyl radicals, such as the methyl, ethyl, n-propyl, iso-propyl, n-butyl, iso-butyl, tert-butyl, n-pentyl, iso-pentyl, neo-pentyl and tert-pentyl radical; alkoxy radicals, such as the methoxy, ethoxy, n-propoxy, iso-propoxy, n-butoxy, iso-butoxy, tert-butoxy, n-pentoxy, iso-pentoxy, neo-pentoxy and tert-pentoxy radical; hexyl radicals, such as the n-hexyl radical; alkenyl radicals, such as the vinyl, allyl, 5-hexenyl, 4-vinylcyclohexyl and the 3-norbornenyl radical; cycloalkyl radicals, such as cyclopentyl, cyclohexyl, 4-ethylcyclohexyl and cycloheptyl radical; norbornyl radicals and methylcyclohexyl radicals; aryl radicals, such as the phenyl, biphenylyl, napthyl, anthryl and phenanthryl radical; alkaryl radicals, such as o-, m- and p-tolyl radical, xylyl radicals and ethylphenyl radical; and aralkyl radicals, such as the benzyl, styryl, and phenylethyl radicals.

Examples of monovalent, substituted radicals are halogenated hydrocarbon radicals, such as the chloromethyl, 3-chloropropyl, 3-bromopropyl, 3,3,3-trifluoropropyl and 5,5,5,4,4,3,3-heptafluoropentyl radical and the chlorophenyl, dichlorophenyl and trifluorotolyl radical; mercaptoalkyl radicals, such as the 2-mercaptoethyl and 3-mercaptopropyl radical; cyanoalkyl radicals, such as the 2-cyanoethyl and 3-cyanopropyl radical; aminoalkyl radicals, such as the 3-aminopropyl, N-(2-aminoethyl)-3-aminopropyl and N-(2-aminoethyl)-3-amino-(2-methyl) propyl radical; aminoaryl radicals, such as the aminophenyl radical; acyloxyalkyl radicals, such as the 3-acryloxypropyl and 3-methacryloxypropyl radical; and hydroxyalkyl radicals, such as the hydroxypropyl radical.

Preferred monovalent radicals are independently selected from $C_1$ to $C_6$ alkyl radicals or the phenyl radical, in particular the methyl, ethyl, propyl or phenyl radical.

Examples of divalent hydrocarbon radicals are linear or branched saturated alkylene radicals, such as the methylene and ethylene radical, as well as propylene, butylene, pentylene, hexylene, cyclohexylene and octadecylene radicals; alkoxyalkylene radicals such as the methoxyethylene and ethoxyethylene radical; unsaturated alkylene or arylene radicals, such as the hexenylene radical and phenylene radicals; alkarylene radicals such as the methylphenylene and ethylphenylene radical, and alkoxyarylene radicals such as the methoxyphenylene and ethoxyphenylene radical. The divalent hydrocarbon radical can be interrupted by divalent radicals, bonded to carbon atoms on both sides, such as —O—, —C(O)O—, —O(O)C—, —CONR$^5$—, —NR$^5$C(O)— and —C(O)—, where $R^5$ is hydrogen or a monovalent, optionally substituted, linear or branched $C_{1-18}$ hydrocarbon radical as described above.

A particularly preferred radical initiator corresponding to the above general formula has:

Hal and Hal'=Br, $R^2$ and $R^3$=methyl and r=0.

The first reaction step involves polymerising a radically polymerisable monomer in the presence of the atom transfer radical initiator. The reaction is catalysed by a Cu(I) salt or other transitional metal species. In this reaction step, the organic halide groups act as initiators in the presence of the radically polymerisable monomers and the catalyst, resulting in the linking of a block of radically polymerisable monomers onto the atom transfer radical initiator by atom transfer radical polymerisation. This block of radically polymerisable monomers constitutes the polymeric block (denoted A) of the polysiloxane block copolymer as described above. The product of the first reaction step is thus a polymer which is end-functionalised with a leaving group capable of nucleophilic substitution by nucleophilic end-groups on a polysiloxane.

The catalyst for the first reaction step is a transition metal salt, preferably a Cu(I) salt such as Cu(I) halide salts (Cl, F, Br, I) and which is preferably complexed to a ligand which is suitable for solubilising the Cu(I) salt in the reaction mixture. WO98/51261 describes preferred ligands for use in solubilising the Cu(I) salt in the reaction mixture (aprotic bidentates such as diphosphates, 2,2' bipyridyl, $C_1–C_{20}$ alkyl substituted bipyridyl and combinations thereof, most preferably 2,2' bipyridyl complexed to a Cu(I) halide salt, in particular CuCl). WO98/51262 also refers to several journal articles which describe examples of the polymerisation process (atom transfer radical polymerisation) used in the second reaction step of the process of the present invention. Further examples of such descriptions can be found in *Polymer* Vol 39, No.21, pp 5163–5170 (Nakagawa et al) and *Macromolecules* 1997, 30, 2190–2193 (Haddleton et al). Those skilled in the art would understand that a variety of other ligands can also be employed.

The polymerisation process of the first reaction step can be furnished in bulk, solution, emulsion and suspension, as would be understood by those skilled in the art.

Radically polymerisable monomers suitable for use in the first reaction step of the process of the present invention are preferably ethylenically unsaturated monomers.

By "polymerisable" is meant monomers that can be polymerised in accordance with the second reaction step of the process of the present invention using atom transfer radical polymerisation, more preferably "living" atom transfer radical polymerisation, in which polymer chain length and architecture can be controlled via stability of the radical, thus leading to improved monodispersity.

By "ethylenically unsaturated" is meant monomers that contain at least one polymerisable carbon-carbon double bond (which can be mono-, di-, tri- or tetra-substituted). Either a single monomer or a combination of two or more monomers can be utilised. In either case, the monomers are selected to meet the physical and chemical requirements of the final polysiloxane block copolymer.

Suitable ethylenically unsaturated monomers have the following general formula:

$$H(R^6)C=C(R^7)(C(O)G$$

in which $R^6$ and $R^7$ are independently selected from hydrogen, $C_1–C_{10}$ straight or branched chain alkyl, methoxy, ethoxy, 2-hydroxyethoxy, 2-methoxyethyl and 2-ethoxyethyl groups;

G is selected from hydroxyl, —O(M)$_{2/v}$, —OR$^8$,13 NH$_2$, —NHR$^8$ and —N(R$^8$)(R$^9$);

where M is a counter-ion of valency v selected from metal ions such as alkali metal ions and alkaline earth metal ions, ammonium ions and substituted ammonium ions such as mono-, di-, tri- and tetraalkylammonium ions, and each R$^8$ and R$^9$ is independently selected from hydrogen, C$_1$–C$_8$ straight or branched chain alkyl, N,N-dimethylaminoethyl, 2-hydroxyethyl, 2-methoxyethyl, and 2-ethoxyethyl. Representative non-limiting examples of monomers useful herein include protected or non-protected acrylic acid and methacrylic acid and salts, esters and amides thereof.

The salts can be derived from any of the common non-toxic metal, ammonium, or substituted ammonium counter ions. The esters can be derived from C$_{1-40}$ straight chain, C$_{3-40}$ branched chain, or C$_{3-40}$ carbocyclic alcohols, from polyhydric alcohols having from about 2 to about 8 carbon atoms and from about 2 to about 8 hydroxyl groups (non-limiting examples of which include ethylene glycol, propylene glycol, butylene glycol, hexylene glycol, glycerol, and 1,2,6-hexanetriol); from amino alcohols (non-limiting examples of which include aminoethanol, dimethylaminoethanol and diethylaminoethanol and their qauaternised derivatives); or from alcohol ethers (non-limiting examples of which include methoxyethanol and ethoxyethanol).

The amides can be unsubstituted, N-alkyl or N-alkylamino mono-substituted, or N,N-dialkyl, or N,N-dialkylamino disubstituted, wherein the alkyl or alkylamino groups can be derived from C$_{1-40}$ straight chain, C$_{3-40}$ branched chain, or C$_{3-40}$ carbocyclic moieties. In addition, the alkylamino groups can be quaternised. Also useful as monomers are protected and unprotected acrylic or/and methacrylic acids, salts, esters and amides thereof, wherein the substituents are on the two and three carbon position of the acrylic and/or methacrylic acids, and are independently selected from C$_{1-4}$ alkyl, hydroxyl, halide (—Cl,—Br,—F,—I), —CN, and —CO$_2$H, for example methacrylic acid, ethacrylic acid, alpha-chloroacrylic acid and 3-cyano acrylic acid. The salts, esters, and amides of these substituted acrylic and methacrylic acids can be defined as described above for the acrylic/methacrylic acid salts, esters and amides. Other useful monomers include vinyl and allyl esters of C$_{1-40}$ straight chain, C$_{3-40}$ branched chain, or C$_{3-40}$ carbocyclic carboxylic acids, vinyl and allyl halides (e.g. vinyl chloride, allyl chloride), (e.g. vinyl pyridine, allyl pyridine); vinylidene chloride; and hydrocarbons having at least one unsaturated carbon-carbon double bond (e.g. styrene, alpha-methylstyrene, t-butylstyrene, butadiene, isoprene, cyclohexadiene, ethylene, propylene, 1-butene, 2-butene, isobutylene, p-methylstyrene); and mixtures thereof.

Preferred monomers useful herein include those selected from protected and unprotected acrylic acid, methacrylic acid, ethacrylic acid, methyl acrylate, ethyl acrylate, n-butyl acrylate, iso-butyl acrylate, t-butyl acrylate, 2-ethylhexyl acrylate, decyl acrylate, octyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, 2-hydroxypropyl acrylate, hydroxypropyl methacrylate, glyceryl monoacrylate, glyceryl monoethacrylate, glycidyl methacrylate, glycidyl acrylate, acrylamide, methacrylamide, ethacrylamide, N-methyl acrylamide, N,N-dimethyl acrylamide, N,N-dimethyl methacrylamide, N-ethyl acrylamide, N-isopropyl acrylamide, N-butyl acrylamide, N-t-butyl acrylamide, N,N-di-n-butyl acrylamide, N,N-diethylacrylamide, N-octyl acrylamide, N-octadecyl acrylamide, N,N-diethylacrylamide, N-phenyl acrylamide, N-methyl methacrylamide, N-ethyl methacrylamide, N-dodecyl methacrylamide, N,N-dimethylaminoethyl acrylamide, quaternised N,N-dimethylaminoethyl acrylamide, N,N-dimethylaminoethyl methacrylamide, quaternised N,N-dimethylaminoethyl methacrylamide N,N-dimethylaminoethyl acrylate, N,N-dimethylaminoethyl methacrylate, quaternised N,N-dimethylaminoethyl acrylate, quaternised N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, fumaric acid, itaconic acid, itaconic anhydride and its half esters, crotonic acid, angelic acid, diallyldimethyl ammonium chloride, vinyl pyrrolidone vinyl imidazole, methyl vinyl ether, methyl vinyl ketone, maleimide, vinyl pyridine, vinyl furan, styrene sulphonate, allyl alcohol, allyl citrate, allyl tartrate, vinyl acetate, vinyl alcohol, vinyl caprolactam and mixtures thereof.

More preferred monomers are those selected from methyl acrylate, methyl methacrylate, methyl ethacrylate, ethyl acrylate, ethyl methacrylate, ethyl ethacrylate, n-butyl acrylate, n-butyl methacrylate, n-butyl ethacrylate, 2-ethylhexyl acrylate, 2-ethylhexyl methacrylate, 2-ethylhexyl ethacrylate, N-octyl acrylamide, 2-methoxyethyl acrylate, 2-hydroxyethyl acrylate, N,N-dimethylaminoethyl acrylate, N,N-dimethylaminoethyl methacrylate, acrylic acid, methacrylic acid, 2-hydroxyethyl acrylate, 2-hydroxyethyl methacrylate and mixtures thereof.

Most preferred monomers are those selected from N,N-dimethylaminoethyl acrylate, N,N-dimethylaminoethyl methacrylate, 2-ethylhexyl acrylate, hydroxyethyl methacrylate, N-octyl acrylamide, 2-hydroxyethyl acrylate, 2-hydroxyethyl methacrylate and mixtures thereof.

Second Reaction Step

The second reaction step involves reacting the polymer obtained from the first reaction step with a polysiloxane having nucleophilic end-groups.

The polysiloxane having nucleophilic end-groups may be linear, branched or hyperbranched, provided it has at least one nucleophilic end-group as described above. Typically such an end-group is one capable of nucleophilic attack via its O, N or S atom.

Examples of preferred polysiloxanes have the formula:

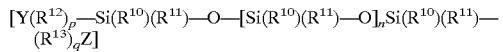

in which n is an integer of 5 to 1,000,000;

R$^{10}$ and R$^{11}$ are independently selected from monovalent, optionally substituted, linear or branched C$_{1-18}$ hydrocarbon radicals as described above, R$^{12}$ and R$^{13}$ are independently selected from divalent, optionally substituted, linear or branched C$_1$–C$_{18}$ hydrocarbon radicals as described above;

p and q are integers having a value of 0 or 1, and

Y and Z are independently selected from hydroxyl, —NH$_2$ and —NHR$^{14}$ where R$^{14}$ is a monovalent, optionally substituted, linear or branched $C_{1-18}$ hydrocarbon radical as described above. Either, but not both, of Y and Z may also be hydrogen or a monovalent, optionally substituted, linear or branched $C_{1-18}$ hydrocarbon radical as described above, thereby giving a mono-end-capped polysiloxane.

Particularly preferred polysiloxanes corresponding to the above general formula have:

n=5 to 1,000,000, preferably 5 to 500;

$R^{10}$ and $R^{11}$=methyl, p and q=0 and Y and Z=hydroxyl; or p and q=1, $R^{12}$ and $R^{13}$=$(CH_2)_3$ and Y and Z=$N_2$.

In the second reaction step, a polysiloxane block copolymer is formed via a nucleophilic displacement reaction between the end-groups on the polysiloxane and leaving groups on the polymer respectively.

The nucleophilic displacement reaction of the second reaction step may be carried out under conventional reaction conditions.

Polysiloxane Block Copolymers

A typical polysiloxane block copolymer obtainable by the process described above is built up from units of the general formula [A]L[B], in which A is a polymeric block built up from radically polymerisable monomer, B is a polysiloxane block and L is a divalent linker group which links the A and B blocks via O—Si, N—Si or S—Si bonds to the B block. Preferably L is selected from:

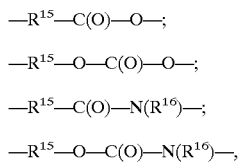

or

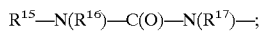

in which $R^{15}$ is a divalent, optionally substituted, linear or branched $C_1$–$C_{18}$ hydrocarbon radical as described above, and $R^{16}$ and $R^{17}$ are independently selected from monovalent, optionally substituted, linear or branched $C_{1-18}$ hydrocarbon radicals as described above.

The overall molecular architecture of the silicone block copolymers of the invention can be described by the formulas A—L—B, A—L—B—L—A, —(A—L—B)$_n$—, wherein n is an integer of 2 or greater, or [A—L—][A—L—]B[—L—A][—L—A], wherein A—L—B represents a diblock structure, A—L—B—L—A represents a triblock structure, —(A—L—B)$_n$— represents a multiblock structure, and [A—L—][A—L—]B[—L—A][—L—A] represents a dendritic structure.

Cosmetic and Personal Care Compositions

The polysiloxane block copolymers of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like. The carriers and additional components required to formulate such products vary with product type and can be routinely chosen by one skilled in the art. The following is a description of some of these carriers and additional components.

Carriers

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin. Carriers suitable for use with hair care compositions of the present invention include, for example, those used in the formulation of hair sprays, mousses, tonics, gels, shampoos, conditioners, and rinses. The choice of appropriate carrier will also depend on the particular copolymer to be used, and whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular copolymer being used, with water, the C1–C6 alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicon derivatives such as cyclomethicone. When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% of the composition. The level of propellant can be adjusted as desired but is generally from about 3% to about 30% of mousse compositions and from about 15% to about 50% of the aerosol hair spray compositions.

Suitable spray containers are well known in the art and include conventional, non-aerosol pump sprays i.e., "atomisers," aerosol containers or cans having propellant, as described above, and also pump aerosol containers utilising compressed air as the propellant.

Where the hair care compositions are conditioners and rinses the carrier can include a wide variety of conditioning materials. Where the hair care compositions are shampoos, the carrier can include, for example, surfactants, suspending agents, and thickeners.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

Additional Components

A wide variety of additional components can be employed in cosmetic and personal care compositions according to the present invention. Examples include the following:

- sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
- anti-dandruff actives such as zinc pyrithione, piroctone olamine, selenium disulphide, sulphur, coal tar, and the like.
- conditioning agents for hair care compositions such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.
- surfactants for hair shampoo and conditioner compositions. For a shampoo, the level is preferably from about 10% to about 30%, preferably from 12% to about 25%, of the composition. For conditioners, the preferred level of surfactant is from about 0.2% to about 3%. Surfactants useful in compositions of the present invention include anionic, nonionic, cationic, zwitterionic and amphoteric surfactants.
- carboxylic acid polymer thickeners. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10–C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners.
- emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate,Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5% of the compositions of the present invention.
- vitamins and derivatives thereof (e.g., ascorbic acid, vitamin E, tocopheryl acetate, retinoic acid, retinol, retinoids, and the like.
- cationic polymers (e.g., cationic guar gum derivatives such as guar hydroxypropyltrimonium chloride and hydroxypropyl guar hydroxypropyltrimonium chloride, available as the Jaguar C series from Rhone-Poulenc).
- preservatives, antioxidants, chelators and sequestrants; and aesthetic components such as fragrances, colourings, hair nutrients and essential oils.

The invention will now be illustrated by the following non-limiting Examples:

EXAMPLE

A silicone block copolymer was prepared by the following process:

Step 1

$Cu^IBr$ (0.0852 g, 0.594 mmol) along with a magnetic stirrer bar was placed in a dry Schlenk flask which was then evacuated and flushed with nitrogen three times. 2-dimethylaminoethyl methacrylate (DMAEMA) (5.0 mL, 0.030 moles), toluene (7.2 mL) and 2-bromoisobutyryl bromide (0.15 mL, 1.19 mmol) were added to the Schlenk using degassed syringes.* The solution was then deoxygenated by three freeze-pump-thaw cycles. Finally, once the flask had reached the desired reaction temperature of 90° C. the $^n$propyl-2-pyridinalmethanimine ligand (1) (0.20 mL, 1.19 mmol) was added with stirring. The reaction mixture immediately turned dark brown in colour on addition of the ligand. The polymerisation reaction was carried out for eight hours.

The monomer was purified by passing down a basic alumina column prior to use and purged with nitrogen for at least one hour. Toluene, which was used as a solvent for all polymerisations, was also degassed in this manner. $Cu^IBr$ was purified before use according to a published procedure.[1]

1) Keller, R. N.; Wycoff, H. D. *Inorganic Synthesis*, 1947, 2, 1.

The product was purified by a conventional dissolution and precipitation method (three times). It had GPC molecular weight of Mn 4,300, Mw 5,200, D 1.18.

Step 2

Poly(dimethyl siloxane) containing hydroxyl groups at both ends (5.6 g, molecular weight 15,000) was dissolved in toluene (100 mL). To this solution, 4-dimethylaminopropylpyridine (0.26 mmol, 0.031 g) was added. Then a solution of the product prepared in Step 1 (3.2 g, Mw 5,200) in toluene (100 ml) was added dropwise over one hour. The reaction was left overnight at room temperature. The reaction mixture was warmed to 50° C. for two more hours to drive the esterification reaction to completion. The solvent was removed under vacuum to yield the block copolymer.

The resultant block copolymer (ABA triblock structure) had a controlled molecular weight and narrow polydispersity.

Tests showed that the copolymer had excellent film-forming, bond strength and sensory properties when formulated into a hairspray.

What is claimed is:

1. A process for making a polysiloxane block copolymer which is built up from units of the formula [A]L[B], in which A is a polymeric block built up from radically polymerisable monomer, B is a polysiloxane block, and L is a divalent linker group, the process comprising the steps of polymerising a radically polymerisable monomer in the presence of an atom transfer radical initiator to form a polymer which is end-functionalised with a leaving group capable of nucleophilic substitution by a nucleophilic end-group comprising an atom selected from the group consisting of oxygen, nitrogen, and sulfur on a polysiloxane, having said nucleophilic end-groups so that a polysiloxane block copolymer is formed via a nucleophilic displacement reaction between the end-groups on the polysiloxane and leaving groups on the polymer respectively.

2. A process according to claim 1, comprising the steps of:
   (i) reacting an atom transfer radical initiator, comprising at least one —C(O)X group, in which X is a leaving group capable of substitution by a nucleophilic O, N or S atom on a polysiloxane and at least one organic halide group capable of generating a radical in the presence of a transition metal catalyst, with radically polymerisable monomers to form a polymer which is end-functionalised with a leaving group capable of nucleophilic substitution by nucleophilic end-groups on the polysiloxane, and
   (ii) reacting the polymer obtained from (i) with a polysiloxane having nucleophilic end-groups so that a polysiloxane block copolymer is formed via a nucleophilic displacement reaction between the end-groups on the polysiloxane and leaving groups on the polymer respectively.

3. A polysiloxane block copolymer prepared by the process of claim 1.

4. A polysiloxane block copolymer according to claim 3, which is built up from units of the general formula [A]L[B], in which A is a polymeric block built up from radically polymerisable monomer, B is a polysiloxane block and L is a divalent linker group which links the A and B blocks via O—Si, N—Si or S—Si bonds to the B block, and which is selected from the group consisting of:

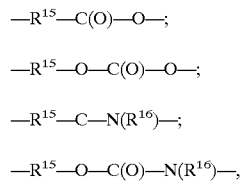

and

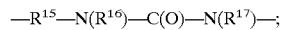

in which $R^{15}$ is a divalent, optionally substituted, linear or branched $C_1$–$C_{18}$ hydrocarbon radical, and $R^{16}$ and $R^{17}$ are independently selected from monovalent, optionally substituted, linear or branched $C_1$–$C_{18}$ hydrocarbon radicals.

5. A cosmetic and personal care composition comprising the polysiloxane block copolymer of claim 3.

6. A cosmetic and personal care composition according to claim 5, which is formulated as a hairspray, gel or mousse.

* * * * *